US008776623B2

(12) United States Patent
Chartier

(10) Patent No.: US 8,776,623 B2
(45) Date of Patent: Jul. 15, 2014

(54) APPARATUS AND METHODS FOR OBTAINING 3-PHASE (LIQUID, GAS AND SOLID) MICROBIOLOGICAL SAMPLES FROM PIPES, PIPELINES, TANKS AND OTHER VESSELS

(75) Inventor: Douglas Maurice Chartier, Saint Charles, MO (US)

(73) Assignees: Douglas M. Chartier; MIC Corrosion Tek, LLC

( * ) Notice: Subject to any disclaimer, the term of this patent is extended or adjusted under 35 U.S.C. 154(b) by 449 days.

(21) Appl. No.: 13/068,319

(22) Filed: May 9, 2011

(65) Prior Publication Data

US 2011/0303025 A1    Dec. 15, 2011

Related U.S. Application Data

(60) Provisional application No. 61/395,195, filed on May 10, 2010.

(51) Int. Cl.
*G01N 1/22* (2006.01)
*G01N 1/04* (2006.01)

(52) U.S. Cl.
USPC .................................. 73/864; 73/864.71

(58) Field of Classification Search
USPC ............ 73/152.23–152.26, 863, 864, 864.33, 73/864.51, 864.71
See application file for complete search history.

(56) References Cited

U.S. PATENT DOCUMENTS

| 4,727,758 | A | * | 3/1988 | Murdock | 73/863.61 |
|---|---|---|---|---|---|
| 5,868,928 | A | * | 2/1999 | Bradley | 210/257.2 |
| 7,478,555 | B2 | * | 1/2009 | Zhan et al. | 73/152.55 |
| 2005/0016302 | A1 | * | 1/2005 | Simpson et al. | 73/865.8 |
| 2007/0050145 | A1 | * | 3/2007 | Zhan et al. | 702/6 |
| 2012/0134140 | A1 | * | 5/2012 | Keatch | 362/101 |

* cited by examiner

*Primary Examiner* — Hezron E Williams
*Assistant Examiner* — Nathaniel Kolb

(57) ABSTRACT

The present invention hereby describes an apparatus and/or apparatuses to collect aqueous solutions, gas compounds, solid compounds and/or hydrocarbon liquid samples from a pipe, pipeline, tank or vessel for microbiological analysis; to determine if that environment contains microbiologically influenced corrosion (MIC) bacterium, which may contribute to the internal wall corrosion of the pipe's, pipeline's, tank's or vessel's metallic composition. The present invention also includes sterile absorbent materials within the apparatus(es); which have different absorbency rates and coatings, which are hydrocarbon and/or aqueous soluble at differing time periods, to represent adequate sampling of the fluids; as it travels through and within a pipe, pipeline, tank or vessel system. Solids are trapped within, and included within, a coated or non-coated sterile matrix which may contain sessilic MIC bacterium. Gas permeates the sterile matrix withholding contained planktonic bacterium thus providing a heterogeneous sampling of the contained contents.

10 Claims, 2 Drawing Sheets

APPARATUS AND METHODS FOR OBTAINING 3-PHASE (LIQUID, GAS AND SOLID) MICROBIOLOGICAL SAMPLES FROM PIPES, PIPELINES, TANKS AND OTHER VESSELS

STATEMENT REGARDING FEDERALLY SPONSORED RESEARCH OR DEVELOPMENT

The rights of the invention are the possession of the inventor, as no federal involvement was present in the invention's research and development.

CROSS-REFERENCE TO RELATED APPLICATIONS

This application claims the benefit of PROVISIONAL APPLICATION No. 61/395,195 filed May 10, 2010.

RELATED U.S. PATENT DOCUMENTS

None of record

FIELD OF INVENTION

The present invention relates to methods and apparatus(es) to sample liquid, gas and solid phases to determine if microbiologically influenced corrosion (MIC) bacteria are present within the phases being transported, stored or otherwise utilized within the void of a metallic pipe, pipeline, tank or vessel. Solids are trapped within a sterile matrix of glass, steel wire or other composition, which may contain MIC bacterium and gas permeates the sterile matrix and absorbents withholding contained planktonic bacterium.

Described herein, among other things, is a self-contained hollow apparatus (es) which is cylindrical, sphere, bullet shaped and/or other three (3) dimensional shape(s); which is inserted into the pipeline, pipe, vessel or tank and is metallic in construction. Within the hollow apparatus (es) there is a containment of various sterile absorbent materials; which either have an affinity for hydrocarbon and/or aqueous solutions or have varying wetting capabilities by the addition of coatings and/or absorbency rates. Thus, they are time sensitive and are exposed within different sections of the pipeline or vessel as the apparatus moves through the structure. Also, within the apparatus is a sterile matrix of glass, steel wire or other composition, which may trap solids as they pass through the apparatus which may contain sessilic MIC bacterium. Also, gas permeates the sterile matrix withholding contained planktonic bacterium as it passes through. The apparatus also contains holes which through the absorbent material and sterile matrix may be inserted into the apparatus. The apparatus serves as a transport collection device for the liquid, gas and solids being sampled.

The sampling device, once contacted with the liquids, gas and solids for analysis is prepared for shipment and shipped to a laboratory for microbiologically influenced corrosion (MIC) bacterium analysis. The laboratory extracts the bacterium, from the absorbent material and sterile matrix; to be analyzed with well known method(s) and allowed to culture in the proper media for the specific bacterium species involved in (MIC) microbiologically influenced corrosion. Once testing is performed, the proper mitigation and abatement methods may be employed, if MIC bacteria are present. The apparatus may also be employed as a monitoring device to determine the effectiveness of MIC corrosion mitigation and abatement procedures.

To the knowledge of the author, no such device(s) exist today for this type of in-situ sample collection of MIC bacterium species from fluid, gas and solid samples contained within pipes, pipelines, tanks and/or vessels.

BACKGROUND OF THE INVENTION

The invention is an improvement on state-of-the-art current devices. The need for the invention is illustrated by a U.S. Federal Highway Administration financed study conducted by C.C. Technologies in 2002 study concluded that the total estimated direct cost of corrosion in the U.S. amounts to $276 billion per year or approximately 3.1% of the gross domestic product (GDP) of the U.S. Flemming, in a separate review, estimates MIC corrosion attributed 20% of overall corrosion cost. This data is quoted from the University of Ohio's Corrosion. Center at: http://www.corrosioncenter.ohiou.edu/nesic/papers/FullText/conference-83.pdf. To further the data collected, one can then extrapolate that MIC corrosion cost 55.2 billion U.S. dollars annually in the United States alone.

The need for the present invention is vividly demonstrated in the oil and gas industry. It has been reported by the SPE (Society of Petroleum Engineers) in paper number 120837-MS at the "SPE International Symposium on Oilfield Chemistry", 20-22 Apr. 2009, The Woodlands, Tex., C. Smith, Lonza, Inc: "Corrosion related transmission pipeline cost estimates convey annual expenditures of $5.4 to $8.6 billion USD distributed among the cost of failures (10%), capital (38%), and operations and maintenance (52%)". Also stated, "Better investigative techniques have recently shown a number of pipeline failures related to MIC and some recent estimates suggest MIC may contribute to as many as 20 to 30 percent of pipeline corrosion failures." This puts the annual total costs for MIC bacterium corrosion in hydrocarbon pipelines in the range of 1.08 billion to 2.58 billion USD/year in the United States alone.

The need for the invention is illustrated by the rapid increase of MIC occurrence within pipelines, tanks and/or vessels in the United States and around the world.

The need for an in-situ sampling device for MIC bacterium is evident since MIC bacterial infection and corrosion is localized in nature and the biofilms, colony types and populations depend on the environmental factors of temperature, pressure, oxygen concentration and nutrient availability in different segments of the pipeline or vessel. Current diagnostic techniques are not designed to determine the existence of such micro, localized corrosion. Mitigation of MIC begins with determining the presence or lack of presence of MIC bacteria. The present invention addresses this need to know through representative sampling of the fluid contained within a pipe, pipeline, tank or vessel. It is a vehicle to deliver to the laboratory the sample to determine MIC bacteria presence in the fluid, gas and solids sampled.

DESCRIPTION OF THE PRIOR ART

Traditional art has included taking liquid samples from the extraction at a valve or access place in the pipe, pipeline, tank or vessel. The sample is then submitted for microbiological analysis to a laboratory. This method has several disadvantages one being determining only the bacterium population at the point of sampling. MIC bacteria are diverse and form biofilms and colonies consisting of varying populations and functions as a combination of aerobic, anaerobic and facilitative bacteria, which all play a part in the final corrosive process. The environmental conditions often dictates which species are viable in a certain area and it is possible to have many different biofilms and colony formations within a very short span of surface area. Therefore, this, "spot sampling" can lead to false negatives and skewed information about the pipe, pipeline, tank or vessel being sampled. New probes have been introduced which contain a media, but they also only identify bacterium at that particular place in the pipeline.

U.S. Pat. No. 5,868,928 by Bruce J Bradley discloses an apparatus which removes bacterium from a surface by vacuum and filters said bacterium from collected fluids, gases and solids. The microfiltration filter can then be submitted to a laboratory for microbiological analysis. This device is useful in certain applications; but may not be used on internal surface areas of tubing or pipe with any length. The device is energy source dependent (110V or battery pack) and is limited to the length of time it is functional to collect samples. Thus, large surface areas cannot be sampled by this device and it is not of proper design for in-situ sampling of pipelines and/or vessels of large size or to be exposed to a flammable environment.

U.S. Pat. No. 4,727,758 by David L. Murdock discloses an apparatus, or pig, to be used in pipelines during phosphoric acid production. This device is useful in the filtration of solids from a slurry stream of phosphoric acid, but may be ineffective at collecting planktonic bacteria from gas and liquid (hydrocarbon and aqueous) phases contained in pipe, pipeline, tanks and/or vessel systems. The device can collect samples of the entire pipe, pipeline, tank and/or vessel depth and/or length, but has no method for sampling according to where it is located in the pipeline. The invention of consideration has the ability to sample at various parts of the pipeline, due to its ability to selectively absorb fluids based on hydrocarbon or aqueous nature and having the ability for time sensitive exposure of the absorbent due to time dissolution of various coatings on the surface of the absorbents. The invention also has the capability to obtain micron size solid particles and the contents of gas which may contain planktonic or sessile MIC bacterium.

SUMMARY OF THE INVENTION

One aspect of the invention is, that the device may be any three dimensional design, but it seems the majority will be either a hollow sphere, or hollow cylinder or hollow bullet shape for ease in usage within pipelines.

Another aspect of the invention is that the device will have holes that penetrate the sphere, cylinder or bullet shape to the internal void within the structure. The holes may be of varied diameters or of the same diameter. The holes serve two functions of the device: 1. To allow liquid, gas and solids to flow through the device as it travels down a pipeline for sampling purposes. 2. To allow an insertion area for the placement of absorbents, and sterile matrix during the manufacture of said device.

Another aspect of the invention is that the absorbents and sterile matrix are designed to fit tightly when placed through the holes on the device thus, preventing loss of materials within the pipeline or vessel.

Another aspect of the invention is that two-hole rubber stoppers will fill the void of the holes, after the absorbents and sterile matrix are added. This will deter accidental discharge of the absorbents and sterile matrix during and after the sampling procedure. Also allowing liquid, solids and gas access into the device for absorption and flow through, as it travels down the pipeline or vessel.

Another aspect of the invention is that the absorbents and sterile matrix length and diameter can be of such dimensions that the use of 2-hole rubber stoppers is not needed. Accidental discharge of absorbents and sterile matrix is highly unlikely. This will increase the flow of the sampled liquid, solids and gas.

Another aspect of the invention is that it will be in a vacuum sealed bag packed for protection against accidental discharge, or atmospheric and handling infection and oxidation of the device, and/or absorbent and/or sterile matrix before usage.

Another aspect of the invention is that it, and its components, will be sterilized with UV lamps emitting 253.7 nanometer wavelengths light and all starting material will be of a sterile nature. The final device will, again, be sterilized with UV lamps before and after vacuum bagging.

Another aspect of the invention is that the absorbents and sterile matrix are of such a design that upon absorption of fluid, solids and gas they will increase in size to the extent that exit from the inside to the outside of the device is not viable. Example: Four inch by four inch 8-ply sterile sponges used in surgery, may be rolled up and inserted within a hole in the device, which can roll out to on its own sheet within the device or when exposed to the fluid, solids and gas being sampled.

Another aspect of the device is that that sterile matrix has varying pore size and porosity to hold and retain particles of various sizes.

Another aspect of the invention is as fluid travels through the device, absorbent material will absorb selective fluid (hydrocarbon, aqueous or both) and bacterium within that fluid.

Another aspect of the invention is that the surface area and construction of the absorbent and sterile matrix will aid in the hosting of the bacterium until extraction has taken place in the laboratory.

Another aspect of the invention is that the absorbents may be enclosed within gelatin capsules or coated with water and/or hydrocarbon soluble compounds such as polyvinyl alcohol (PVA) and others to deter absorbent exposure and increase time before exposure while traveling down a pipeline or vessel. Various thickness and composition of the coatings will be employed to determine solubility time of the created capsules or devices. This will allow differential sampling as the apparatus travels down a pipeline.

Another aspect of the invention is that the absorbent's time release factor may depend on the coating's thickness and temperature activation. Example: PVA film having a solubility taking effect after exposure to 80-85 degrees centigrade.

Another aspect of the invention is the absorbent may be coated by being sprayed, dipped or covered with a film sheet of varying thickness and temperature dependant solubility; in singular or combined methods.

Another aspect of the invention is that the device may be custom engineered for the individual pipeline being sampled. Example: Calculations of velocity vs. length indicate an area of the pipeline which takes a substantial increase in pipeline's depth and rises to normal depth within a certain length segment, demands sampling to be taking place 10 minutes to 13 minutes within the apparatus run. It is known that this area is a prime area for produced water to gather and condensation to occur. Such an area is excellent for the growth of MIC bacterium, as the bacteria and nutrients may be available within this stretch of pipeline. Exposed aqueous absorbents are designed, with various coatings, to absorb within this area, based upon calculations of velocity vs. time of solubility of coatings.

Another aspect of this invention is that the sterile matrix may be coated with an aqueous or hydrocarbon coating of various solubility, thickness and temperature sensitivity to allow timed exposure for solid and gas content collection purposes.

Another aspect of the invention is that it should be made evident that the primary device design is mainly is to determine if MIC bacterium exists within the totality of length of the pipeline tested and not to pinpoint where the colonies or biofilm may actually be. MIC bacterium presence, or not, determination is valuable information as infection of the pipeline anywhere in the pipeline may, and probably will, result in localized pitting corrosion and reduction of the pipeline's integrity as a whole. Great environmental damage and personal injury or death may result from "pinhole" leaks and a chance of explosion from natural gas pipelines.

Another aspect of the invention is that upon sample completion, the apparatus may be enclosed from access by sterile plugs for the holes and placed in a sterile bag. This limits the effects of oxygen on the contents of the apparatus and oxygen exposure to bacterium. All handling of the device should be done with sterile latex gloves. The invention should be packaged accordingly to UN, DOT, local code and laws for transport. Sample should be submitted to a microbiological laboratory within seventy-two (72) hours of sampling. Once received, bacteria will be extracted from the device with well-known laboratory extraction procedures. Colonization of the specific bacterium will be accomplished on specific bacterium groups known to be active in MIC corrosion. Some of the groups which are active in the MIC process are: Acid Producing Bacterium (APB), Sulfate Reducing Bacterium (SRB) Heterotrophic (HAB) and Iron Related Bacterium (IRB). Biological medium is commercially available to test for these groups quantitatively and qualitatively. Report will be issued, upon completion, and delivered to the company's personnel responsible for their corrosion monitoring and mitigation of pipelines and vessels.

Another aspect of the invention is that it may be used in naturally occurring waters: rivers, lakes, streams oceans and seas, to determine the random sampling of MIC bacteria.

Another aspect of the invention is that it may be used in pipelines or vessels for processed chemicals, natural gas, oil, diesel fuel, aviation fuel and other liquids; for the sampling of MIC bacteria within those pipelines.

Another aspect of the invention is that petroleum refineries, gas and oil pipelines and vessels may use invention to sample various process stages and discover if process interfering, "Black Powder" is present and/or microbiologically derived from sulfate reducing bacterium and other microbiologically influenced corrosion bacteria.

Another aspect of the invention is that it may be used in manufacturing process fluids, tanks, wells and other holding vessels for the presence of MIC bacteria.

Another aspect of the invention is that it may be used in nuclear power plants, conventional power plants, manufacturing process fluids, ships, boats, ballast tanks, fire sprinkler systems, cooling towers, refineries, storage depots and other commercial processes to determine if MIC bacteria are present.

Another aspect of the invention is that it may be used to diagnose corrosion problems by the addition or subtraction of MIC bacteria being a consideration for the corrosive source.

Another aspect of the invention is that it is environmentally neutral, as the device may be sterilized, after use, and recycled.

Another aspect of the invention is that it is easy for both the layman and scholar to use and receive accurate results by its use.

BRIEF DESCRIPTION OF DRAWINGS

FIG. (001): The present invention hereby describes a specific apparatus(es) to collect aqueous solutions and/or hydrocarbon liquid samples from a pipe, pipeline, tanks and other vessels for a microbiological influenced corrosion (MIC) bacterium.

FIG. (002): The present invention also includes sterile absorbent materials within the apparatus(es) which have different absorbency rates and coatings which are soluble at different times to represent adequate sampling of the contained fluids.

DETAILED DISCLOSURE OF THE INVENTION EMBODIMENT(S)

Figure 1:
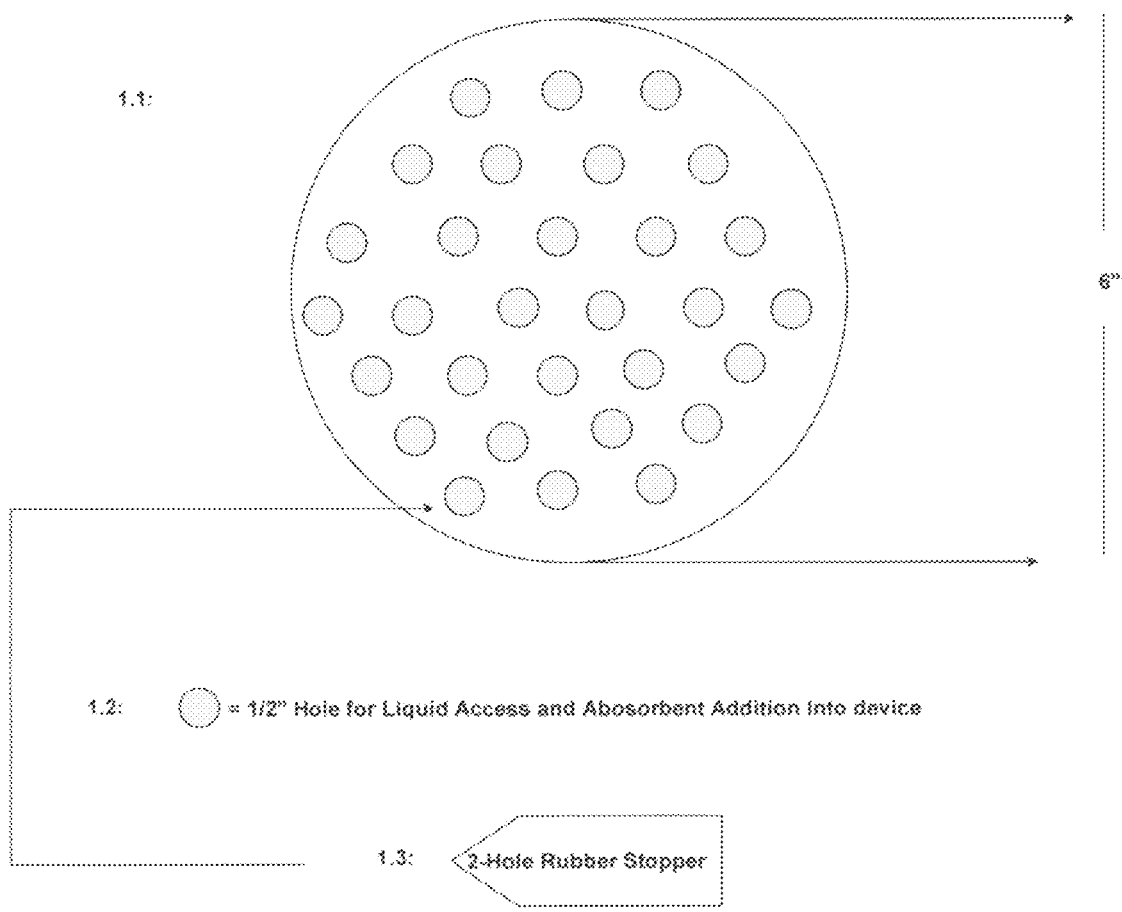

In an embodiment the apparatus is made of stainless steel or black iron.

In an embodiment the apparatus is made of aluminum.

In an embodiment the apparatus is made of plastic.

In an embodiment the apparatus is made of copper.

In an embodiment the apparatus is made of Styrofoam.

In an embodiment the apparatus is made of brass.

In an embodiment the apparatus is made of galvanized iron.

In an embodiment the apparatus is made of carbon composite.

In an embodiment the apparatus is a hollow sphere.

In an embodiment the apparatus is cylindrical in shape and hollow.

In an embodiment the apparatus is cone or bullet shaped and hollow.

In an embodiment the apparatus is coned or bullet shaped with ridges and/or wings which contact the wall of the pipe scraping the surface and cleaning the internal piping.

In an embodiment the apparatus is pancake shaped and hollow.

In an embodiment the apparatus may be rod shaped and hollow.

In an embodiment the absorbent and sterile matrix may be enclosed in a small bag of permeated plastic, burlap, or other material.

In an embodiment the absorbent may be contained in a gelatin capsule.

In an embodiment the absorbent may be contained in a gelatin capsule coated with polyvinyl alcohol (PVA).

In an embodiment the absorbent may be contained in a gelatin capsule coated with PVA and then inserted into another gelatin capsule coated with PVA.

In an embodiment the absorbent may be contained in a gelatin capsule which may or may not be coated with PVA and then inserted into another gelatin capsule which may or may not be coated with PVA.

In an embodiment the absorbent may be coated with a polyvinyl alcohol-gelatin hydrogel.

In an embodiment the absorbent may be sterile surgical sponges.

In an embodiment the absorbent may be sterile carbon nanotubes.

In an embodiment the absorbent may be sterile aluminosilicate nano-particles.

In an embodiment the absorbent may be sterile zeolites.

In an embodiment the absorbent may be sterile natural sponge.

In an embodiment the absorbent may be sterile synthetic sponge.

In an embodiment the absorbent and/or coating may be; sterile guar, single, double or triple derived.

In an embodiment the absorbent may be and/or coating; sterile cellulose, single, double or triple derived.

In an embodiment the absorbent may be sterile gauze.

In an embodiment the absorbent may be sterile activated carbon.

In an embodiment the absorbent and/or coating may be; sterile high molecular weight polyvinyl alcohol (PVA) sponge.

In an embodiment the absorbent and/or coating; may be sterile gelatin.

In an embodiment the absorbent and/or coating may be sterile starch and its derivatives.

In an embodiment the absorbent and/or coating may be sterile gum Arabic.

In an embodiment the absorbent and/or coating may be sterile methylcellulose.

In an embodiment the absorbent and/or coating may be sterile sodium polyacrylate.

In an embodiment the absorbent and/or coating may be sterile potassium polyacrylate.

In an embodiment the absorbent and/or coating may be sterile calcium polyacrylate.

In an embodiment the absorbent may be sterile bentonite clay.

in an embodiment the absorbent may be sterile illite clay.

In an embodiment the absorbent may be sterile chlorite clay.

In an embodiment the absorbent may be sterile cellulose actophthalate.

In an embodiment the absorbent may be sterile cross-linked starch-g-polyacrylae.

In an embodiment the absorbent may be sterile vermiculite.

In an embodiment the absorbent may be a sterile perlite.

In an embodiment the absorbent may be sterile cotton.

In an embodiment the absorbent may be sterile wool.

In an embodiment the sterile matrix may be made of spun iron fibers.

In an embodiment the sterile matrix may be made of spun glass fibers.

In an embodiment the sterile matrix may be made of spun PVC fibers.

In an embodiment the sterile matrix may be made of spun CPVC fibers.

In an embodiment the sterile matrix may made of spun aluminum fibers.

In an embodiment the sterile matrix may be made of high molecular weight PVA sponge.

In an embodiment the sterile matrix may made of spun carbon fiber wire.

DESCRIPTION OF THE PREFERRED EMBODIMENT(S)

The apparatus (es) may be ½ inch to 18 inch in diameter, according to the needs of the system. It may contain equally spaced holes from 1/16" to 1½" in diameter and the holes should cover from 1/16$^{th\ to}$ ⅔rds of the total surface area of the outside of the device. It may contain a hook or eyelet for retrieval from tanks, vessels, etc and it may not. Its use in pipelines may be before, after and/or in between traditional pigging units or as a stand alone pigging device. The main purpose of the invention is to gather samples of bacteria from various fluids, solids and gases throughout the pipe, pipeline, tank or vessel and be shipped to a certified laboratory for quantitative and qualitative analysis of microbiologically influenced corrosion bacterium species. Upon the completion of such testing, a full written report will be issued for the client to determine what type of remediation and abatement methods may be used and for continuous monitoring of said assets.

The device can be made of aluminum, copper, brass or steel to withstand the pressure exposure and sudden decrease in velocity it may experience at the receiver or collection device at the end of the pipeline or vessel.

The invention may be used in tanks to sample different levels of the tank and or vessel for bacterium activity. To sample the top of a tank or vessel, the invention may be made of an organic substrate which has a specific gravity of less then (<) 1.00. Such a device may be made from available cross-linked polymers (plastic) and carbon structures of low density. Different oxygen levels determine what type of microbiologically influenced corrosion (MIC) bacterium may be present, as some are aerobic (air breathing) and others are anaerobic (air hating). Different colonies and biofilms may exist on the top of the tank and or vessel then those viable on the bottom of the tank and or vessel and the integrations throughout the tank and or vessel. To sample the bottom of a tank and/or vessel containing aqueous fluids larger than (>) 1.00 specific gravity material may be suspended by a hook or eyelet with a rope or other retrieval device, at the bottom of the tank and or vessel. After sufficient time for the sampling to occur, the device may be retrieved and sent in for analysis. By using sterile absorbents and matrix, which have been prepared with or without time released coatings, a precise microbiological sampling of the bottom's microbiological content may be achieved.

DETAILED DESCRIPTION OF THE DRAWINGS

FIG. 1: Is a drawing of a specific apparatus (exemplary) which falls into the guidelines of the apparatus description of the invention.

FIG. 1.1: Is a 6" diameter hollow aluminum sphere with approximate wall thickness of ⅛", this item is commercially available from a number of manufacturers.

FIG. 1.2: Are ⅝" holes drilled through the wall of the sphere completely through to the void within the sphere. These holes are drilled with a conventional drill press and a ⅝" hole saw available commercially from a number of manufacturers. The holes are spaced 1.5" apart and cover the entire surface of the sphere. The holes serve the purpose of having an access point to insert the absorbents and sterile matrix and allow flow through the apparatus during the sampling procedure.

FIG. 1.3: Are optional #1 2-hole laboratory rubber stoppers. The holes are 3 mm. in diameter. Their purpose is to contain absorbents while allowing fluid through the apparatus.

Figure 2:
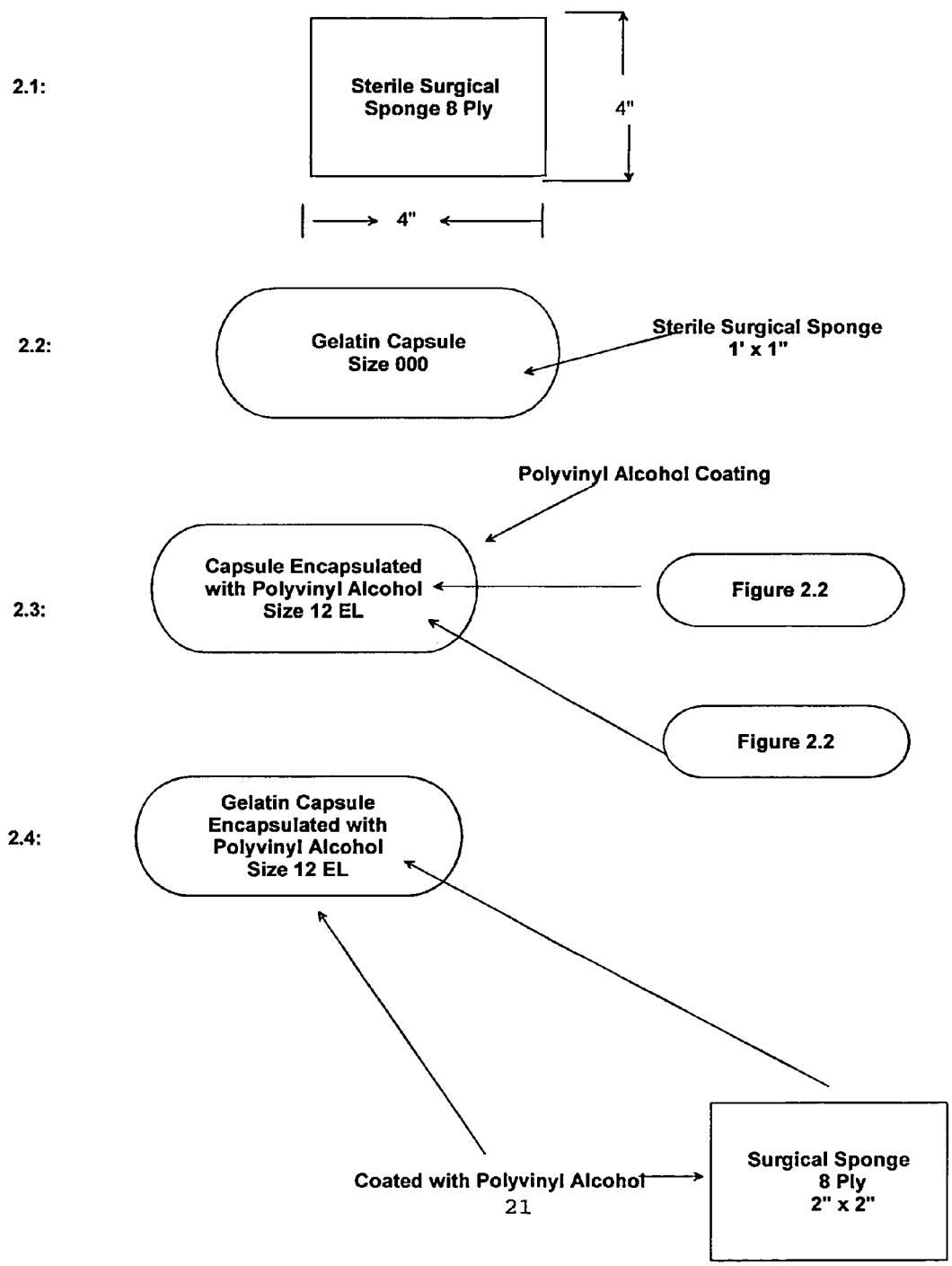

FIG. 2: FIG. 2 is an exemplary construction of four (4) different types of absorbents used in the apparatus described in the invention.

FIG. 2.1: 4"×4" sterile surgical sponge. Is surgical sponge is 8-ply and available from many medical supply companies. It is absorbent to hydrocarbon and aqueous solutions and it is absorbent upon immediate contact with fluid.

FIG. 2.2: Is a sterile gelatin capsule size 000 and inserted inside is a 1"×1" sterile surgical sponge. The gelatin capsule is soluble only in aqueous solutions and absorption of the sterile surgical sponge is retarded in time, due to the solubility rate of the gelatin capsule. This design offers aqueous solubility only and initial coating dissolution before aqueous solution is absorbed by the sterile surgical sponge. Both components are commercially available by numerous medical supply companies.

FIG. 2.3: Is a sterile gelatin capsule size 12 EL. The capsule will hold 2 each of FIG. 2.2. Solubility time extension is achieved by coating the size 12 EL with different thicknesses of polyvinyl alcohol. Polyvinyl alcohol is aqueous soluble only and the thickness of the coating can control the solubility rate to expose the two (2) FIG. 2.2 components. The design of the FIG. 2.2 components will add dissolution time to expose the sterile surgical sponges. Delay of exposure of sterile surgical sponges will aid in taking biological samples further down the length of the pipeline being tested. All components of this design are available through numerous medical supply companies and commercial chemical suppliers.

FIG. 2.4: Is a sterile gelatin capsule size 12 EL. The capsule will hold a rolled 2"×2" sterile surgical sponge, which has been saturated with polyvinyl alcohol and coated, externally, with polyvinyl alcohol, of various thicknesses. The sterile sponge is then inserted into the sterile gelatin capsule, size 12 EL, and the capsule is then coated with various thicknesses of polyvinyl alcohol. The control of thickness of the polyvinyl alcohol coating on the sterile gelatin capsule and also the thickness of the polyvinyl alcohol coating on the 2"×2" sterile 8-ply surgical sponge; will result in delayed absorption of aqueous solution and give added time for sample collection further in distance of the subjective pipeline being sampled for microbiological species.

FIG. 2.1 thru FIG. 2.4 may be inserted within FIG. 1.1 in varied quantities, as desired, to stage microbiological sampling within the fluid contained at various points within the pipeline being sampled. These devices may be custom designed according to the parameters of an individual pipeline, tank or vessel.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An in-situ sampling apparatus for microbiologically influenced corrosion (MIC) bacterium to be used in pipes, pipelines, or tanks to determine if the pipe, pipeline, or tank has the presence of MIC bacterium; wherein after sampling is accomplished, the apparatus is sent to a certified laboratory to determine, by standard testing procedures, if MIC bacterium are present, quantitatively or qualitatively; the apparatus has been designed to sample liquids (both hydrocarbon and aqueous), gas for planktonic bacterium and solids to determine sessilic bacterium;
whereon the improvement is composed of three major components: a three-dimensional vessel, sterile absorbents coated with time dependent soluble coatings for increment sampling and a sterile matrix with or without coatings to obtain MIC bacterium and solids as the device travels through the phases contained within the pipe, pipeline, or tank.

2. The apparatus of claim 1, wherein the vessel has scraping devices in addition to its primary function of sampling; the scraping, sampling apparatus may be winged, ridged or have brushes mounted on the exterior wall of the apparatus to clean the internal surface of the pipes, pipelines, or tanks as it travels through aforementioned pipes, pipelines, or tanks; allowing dynamic sampling and cleaning.

3. The apparatus of claim 1, wherein the vessel is hollow and has ingress and egress ports for liquids, solids and gases.

4. The apparatus of claim 1, wherein the composition of the vessel may be plastic, fiberglass, aluminum, stainless or mild steel, iron, copper, brass, bronze, galvanized, silicon-carbide, carbon fiber, or ceramic in constitution; or any combination of aforementioned constitutions.

5. The apparatus of claim 1, wherein the sterile absorbents may be constituted of gauze, cotton, filter paper activated carbon, natural and synthetic sponges, clays, carbon nanotubes, aluminosilicate nanoparticles, modified and natural starch, zeolite; guar single, double or triple derived; cellulose single, double or triple derived; polyvinyl alcohol, gelatin Arabic gum, methylcellulose, wool, fabric, cellulose actophthalate, cross-linked starch-g-polyacrylate, perlite vermiculite or any combination of aforementioned compounds.

6. The apparatus of claim 1, wherein the sterile absorbent coating may be constituted of aqueous soluble polymers and compounds; hydrocarbon soluble polymers and compounds; permeated plastic bag, burlap bag, cloth bag, gelatin capsules, polyvinyl alcohol (PVA), polyvinyl alcohol coated gelatin capsules, a polyvinyl alcohol-gelatin hydrogel; sterile guar, single, double or triple derived; sterile cellulose, single, double or triple derived; gelatin, starch and its derivatives, Arabic gum, methylcellulose, sodium polyacrylate, potassium polyacrylate, sugar, calcium polyacrylate, cellulose actophthalate, cross-linked starch-g-polyacrylate or any combination of aforementioned compounds.

7. The apparatus of claim 6 wherein the sterile absorbent coating comprises several layers or combinations of layers of compounds to control dissolving time of the coatings on the absorbents thus creating time dependent exposure of absorbent components and controlled sampling of phases as the apparatus proceeds through the pipe, pipeline, or tank.

8. The apparatus of claim 1, wherein the sterile matrix is composed of one or any combination of the following fiber matrix structures: spun iron, spun glass, high molecular weight PVA sponge, spun fiberglass, spun polyvinyl acetate, spun chloride polyvinyl acetate, spun ethylene-vinyl acetate, spun polyacrylonitrile, spun polyesters, spun polyamides, spun polyolefins rods, plastic or glass spheres, nylon spheres, ceramic spheres wood fibers, or any combination of aforementioned compounds.

9. The apparatus of claim 1, wherein the sterile matrix coatings may be constituted of aqueous soluble polymers and compounds; hydrocarbon soluble polymers and compounds; permeated plastic bag, burlap bag, cloth bag, gelatin capsules, polyvinyl alcohol (PVA), polyvinyl alcohol coated gelatin capsules, a polyvinyl alcohol-gelatin hydrogel; sterile guar, single, double or triple derived; sterile cellulose, single, double or triple derived; gelatin, starch and its derivatives, Arabic gum, methylcellulose, sodium polyacrylate, potassium polyacrylate, sugar, calcium polyacrylate, cellulose actophthalate, cross-linked starch-g-polyacrylate or any combination of aforementioned compounds and may be composed of several layers or combinations of coatings of aforementioned compounds on the sterile matrix.

10. A method to collect samples from specific areas of a pipe, pipeline, or tank by time controlled selective absorbents comprising the steps of:

selecting sterile absorbents coated with one or more soluble coatings that will dissolve after one or more predetermined time periods;

placing said coated sterile absorbents in a hollow vessel along with a sterile matrix;

allowing the vessel to flow through a pipe, pipeline, or tank;

retrieving the vessel;

testing the absorbent and matrix for MIC bacteria; and determining one or more locations of MIC bacteria in the pipe, pipeline, or tank based on the one or more predetermined time periods associated with the one or more soluble coatings.

\* \* \* \* \*